United States Patent [19]

Howarth

[11] 4,225,503
[45] Sep. 30, 1980

[54] MANUFACTURE OF ESTERS

[75] Inventor: Michael S. Howarth, Manchester, England

[73] Assignee: Imperial Chemical Industries Limited, London, England

[21] Appl. No.: 951,259

[22] Filed: Oct. 13, 1978

[30] Foreign Application Priority Data

Nov. 28, 1977 [GB] United Kingdom ............... 49348/77

[51] Int. Cl.$^3$ ................. C07C 69/743; C07C 69/747; C07C 120/00
[52] U.S. Cl. ................................. 260/465 D; 560/124
[58] Field of Search .................... 560/124; 260/465 D

[56] References Cited

U.S. PATENT DOCUMENTS 2,822,348  2/1958  Haslam .................. 560/234

FOREIGN PATENT DOCUMENTS 7704073 10/1977 Netherlands ............................ 560/124
7704074 10/1977 Netherlands ............................ 560/124
 970431  9/1964 United Kingdom .................... 560/234

Primary Examiner—Natalie Trousof
Assistant Examiner—Michael Shippen
Attorney, Agent, or Firm—Cushman, Darby & Cushman

[57] ABSTRACT m-Phenoxybenzyl esters of carboxylic acids are prepared from the methyl or ethyl esters of the acids by reaction of the latter with m-phenoxybenzyl alcohol in the presence of a transesterification catalyst of the formula $Ti(O.CO.R)_2Z_2$ in which R is a hydrocarbon radical and Z is a bidentate chelate compound.

7 Claims, No Drawings

MANUFACTURE OF ESTERS

This invention relates to an improved process for the manufacture of esters and more particularly to the manufacture of esters of m-phenoxybenzyl alcohol.

A number of esters of m-phenoxybenzyl alcohol are of insecticidal value, for example, those with certain substituted 2,2-dimethylcyclopropane carboxylic acids. These esters may be prepared from the corresponding acids by converting the latter into the acid chloride which may then be reacted with m-phenoxybenzyl alcohol. The cyclopropanecarboxylic acids are conveniently isolated in the form of their methyl and ethyl esters, and the latter provide an alternative route to the corresponding m-phenoxybenzyl esters, which can conveniently be obtained from the methyl or ethyl esters by an ester interchange reaction with m-phenoxybenzyl alcohol or certain derivatives thereof, in the presence of an ester interchange catalyst.

Sodium methoxide or sodium ethoxide may be used as a transesterification catalyst in the conversion of the methyl or ethyl esters of carboxylic acids into their esters with m-phenoxybenzyl alcohol or its α-cyano or α-ethinyl derivative. These sodium alkoxides are effective catalysts, but when pyrethrin type esters of cyclopropane carboxylic acids are involved its use may adversely influence the cis/trans-isomer ratio in the direction of the less insecticidally-active trans isomer.

Tetramethyl- or tetraethyl titanate may be used as a transesterification catalyst in the conversion of the methyl or ethyl esters of carboxylic acids into their esters with m-phenoxybenzyl alcohol or its α-cyano or α-ethinyl derivative.

Tetramethyl- or tetraethyl titanate may also be used to catalyse the ester interchange reaction between esters of m-phenoxybenzyl alcohol, and α-cyano or α-ethinyl derivatives thereof, with carboxylic acids $R.CO_2H$ wherein R is an alkyl group containing not more than 3 carbon atoms, and the methyl or ethyl ester of a carboxylic acid containing at least 6 carbon atoms, especially a 2,2-dimethylcyclopropanecarboxylic acid. These tetra-alkyl titanates do not affect the cis/trans isomer ratio of pyrethrin-type esters of cyclopropane carboxylic acids. However, the tetra-alkyl titanates are very reactive towards water, and because of this their quality is variable according to whether or not they have been freshly prepared and to the extent to which they have been excluded from contact with moisture. Poor quality catalyst may adversely affect the ester interchange reaction, leading to the formation of by-products, with consequent reduction in the purity and yield of the desired esters.

Transesterification catalysts of diol or polyol titanates or of a chelate compound of titanium may be used with a diketone or a β-ketoester, any residual valencies on the titanium atom being satisfied by a diol, a polyol, OH or OR in which R is a lower alkyl group. Many of these catalysts have the advantage over tetramethyl- or tetraethyl titanate that they are not sensitive to moisture, so that the catalysts need not be freshly prepared or the other reactants and/or solvents specially dried. However, these catalysts do require the use of reaction temperatures in the region of 170° C. for transesterification to proceed at a reasonable rate, and when thermally sensitive reactants are involved such temperatures may lead to decomposition with consequent loss of yield and quality of the desired product and to the formation of undesirable by products.

According to the present invention there is provided a process for the preparation of esters of m-phenoxybenzyl alcohol and its α-cyano and α-ethinyl derivatives with carboxylic acids which comprises mixing a methyl or ethyl ester of the carboxylic acid, m-phenoxybenzyl alcohol or its α-cyano or α-ethinyl derivative and a transesterification catalyst which is a titanium compound of the formula

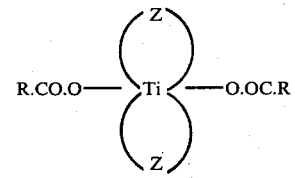

wherein R is a hydrocarbon radical and Z is a bidentate chelate compound, and heating the mixture at a temperature such that the methanol or ethanol are removed by distillation as they are formed.

The catalysts defined above and processes for their preparation constitute further features of the invention.

The hydrocarbon radical R may be an alkyl, cycloalkyl, aralkyl or aryl radical. It is preferred that R is an alkyl radical and further preferred that it is a lower alkyl radical. Examples of cycloalkyl, aralkyl and aryl radicals represented by R are cyclohexyl, benzyl and phenyl respectively.

Examples of the bidentate chelate compounds represented by Z are acetylacetone and ethyl acetoacetate.

The titanium catalysts having the above-defined formula may be obtained by reaction of a tetra-alkyl titanate $Ti(OR^1)_4$ in which $R^1$ is a lower alkyl group, with an acid anhydride $(R.CO)_2O$ wherein R has the meaning defined above, to give the corresponding compound $Ti(O.OC.R)_2(OR^1)_2$, which is subsequently reacted with 2 moles of the bidentate chelate compound Z to give $Ti(O.OC.R)_2Z_2$.

Alternatively, the tetra-alkyl titanate $Ti(OR^1)_4$ may be reacted with 2 moles of the bidentate chelate compound Z to give $Ti(OR^1)_2Z_2$, which is subsequently reacted with 2 moles of an acid $R.CO_2H$, wherein R has the meaning defined above, to give $Ti(O.OC.R)_2Z_2$.

The term "lower alkyl" in this specification means an alkyl group containing from 1 to 4 carbon atoms.

The catalyst preparations described above are carried out in an inert solvent for the tetraalkyltitanate, for example, an aliphatic petroleum fraction such as a petroleum ether having a boiling range of 100°–120° C.

A preferred tetra-alkyl titanate for use in the preparation of the catalysts is tetraisopropyl titanate.

In carrying out the process of the invention, the ingredients may be mixed in any order and the mixture, preferably stirred or otherwise agitated, is raised to the reaction temperature. This temperature is generally the same as that required when tetramethyl- or tetraethyl titanate is used as the catalyst, and reaction will usually proceed satisfactorily at a temperature in the range 140°–150° C., although temperatures lower or higher than this range may also be used when circumstances require.

If desired a solvent may also be used, especially one which gives a reaction mix boiling at the desired reaction temperature so that the methanol or ethanol formed during the process is distilled off with a part of the solvent.

Suitable solvents are for example hydrocarbons such as toluene or methylcyclohexane, halogenated hydrocarbons wherein the halogen atom is inert under the reaction conditions, e.g. chlorinated aromatic hydrocarbons such as chlorobenzene, and ethers such as dioxan. Lower boiling solvents such as cyclohexane may be used but need a longer reaction period at atmospheric pressure.

The catalysts the use of which is within the scope of the present invention are not sensitive to moisture, and consequently it is not necessary for any of the reactants, or solvents if used, to be especially dry.

The amount of catalyst used is at least 0.0005 Mol., and preferably from 0.001–0.2 Mol per mol., of carboxylic ester.

The required proportions of m-phenoxybenzyl alcohol or its α-cyano or α-ethinyl derivative and methyl or ethyl ester of carboxylic acid are equimolar. Excess of either reactant may be used if desired and may generally be recovered unreacted at the end of the process, for example by distillation under reduced pressure.

The ester produced by the process of the invention may be isolated by any convenient procedure, for example by removing the solvent, if any, and any unchanged reactant, by distillation to leave the crude ester which may be purified by conventional means suitable for the ester concerned. If the reaction is carried out in an inert organic solvent such as petroleum ether, the reaction mixture, after completion of the reaction, may be treated with an acid, for example, hydrochloric acid, to precipitate the catalyst, which is then removed by filtration. The solvent and any other volatile materials may then be removed from the filtrate, conveniently under reduced pressure, to leave the desired ester, which usually requires no further purification.

The methyl or ethyl ester of a carboxylic acid which may be used in the process of the invention is any of such esters which has a boiling point significantly higher than the reaction temperature. Such esters may be derived from aliphatic, aromatic, cycloaliphatic or heterocyclic carboxylic acids but the process of the invention is of particular value for the manufacture of m-phenoxybenzyl, and α-cyano and α-ethinyl-m-phenoxybenzyl esters of insecticidal activity, for example from 4-methyl-α-isopropylphenylacetic acid or more especially of pyrethrin-type esters of 2,2-dimethylcyclopropanecarboxylic acids.

Examples of these latter are particularly esters of 2,2-dimethylcyclopropanecarboxylic acids containing in the 3- position substituted vinyl groups such as 2',2'-dimethylvinyl, 2',2'-dichlorovinyl, 2'-ethylvinyl, 2',2'-dibromovinyl, 2'-chloro-2'-trifluoromethylvinyl and 2',2'-bis-(trifluoromethyl)vinyl. These acids are normally obtained as mixtures of cis and trans forms, which in the case of the desired m-phenoxybenzyl esters have different insecticidal potency. The process of the invention is particularly valuable in that it brings about a minimum of interconversion of the cis into the less potent trans forms and also lower formation of by-products. The process also has the advantage that in general it gives a greater conversion of the methyl or ethyl esters into pyrethrin-type esters of cyclopropane carboxylic acids compared with the comparable processes in which the catalyst is tetramethyl or tetraethyl-titanate, sodium methoxide or sodium ethoxide.

The invention is illustrated but not limited by the following Examples in which all parts and percentages are by weight.

EXAMPLE 1

Preparation of catalyst 85.2 parts of isopropyl titanate in 100 parts of petroleum ether boiling point 100°–120° C., are treated with 61.3 parts of acetic anhydride using external cooling to maintain the temperature below 40° C. The mixture is stirred and boiled under reflux for one hour and then distilled, the solvent collected being replaced at the same rate with fresh petroleum ether added to the reaction mixture until 400 parts of distillate have been collected. 60 parts of acetylacetone are then added to the stirred mixture at the boil. After cooling, the precipitate is collected, washed with petroleum ether, and dried to give 33.6 parts of product.

EXAMPLE 2

Preparation of catalyst 14.2 parts of isopropyl titanate in 16 parts of petroleum ether boiling point 100°–120° C. are treated with 10 parts of acetylacetone in 50 parts petroleum ether. The temperature is maintained at less than 40° C. by external cooling. The mixture is stirred at room temperature for 2 hours, then a solution of 17.6 parts n-butyric acid in 25 parts of petroleum ether is added, followed by boiling the mixture under reflux for 2 hours, and then cooling and filtering to obtain a yellow product which is washed with petroleum ether and dried to give 6 parts of product.

The 17.6 parts of n-butyric acid used in the above preparation may be replaced by 17.6 parts of isobutyric acid when a similar product is obtained.

EXAMPLE 3

Use of catalyst in transesterification reaction 2.5 Parts of the catalyst prepared in Example 1 are added to a rapidly stirred mixture of 244.1 parts of ethyl 2,2-dimethyl-3-(2',2'-dichlorovinyl)cyclopropane carboxylate (strength 97.1%; cis:trans isomer ratio 41.2:58.8), 205.1 parts of 3-phenoxybenzyl alcohol (strength 97.5%) and 50 parts of technical toluene. The stirred solution is raised to the boiling point, corresponding to a temperature of 146° C. in the mixture and the volatile material is distilled out of the reaction vessel. The material distilling out of the reaction is replaced by injecting technical toluene into the reaction mixture via an inlet opening below the surface of the reaction mixture. The toluene is injected by a metering pump at the same rate approximately as distillate is collected (approximately 200 parts per hour).

After the reaction has been proceeding for 13½ hours at 144°–147° C. analysis indicates that it is virtually complete and the mixture is cooled to 100° C. 9 Parts of 10% hydrochloric acid are added and the stirred mixture is allowed to cool to room temperature. The mixture is filtered to remove the precipitated catalyst and the filtrate is evaporated under vacuum to remove the toluene and other volatile compounds. The product so obtained (390 parts) contained 91.4% of 3-phenoxybenzyl 2,2-dimethyl-3-(2',2'-dichlorovinyl)cyclopropane carboxylate of cis:trans isomer ratio 38.6:61.4, and 1.7% of 3-phenoxybenzyl alcohol.

EXAMPLE 4

Use of catalyst in transesterification reaction

The experiment in Example 3 is repeated using 2.5 parts of the n-butyryl catalyst from Example 2.

The reaction temperature is 147°–149° C. for 15 hours, and the final product (390 parts) contains 88.9% of 3-phenoxybenzyl 2,2-dimethyl-3-(2',2'-dichlorovinyl)cyclopropane carboxylate of cis:trans isomer ratio 38.5:61.5, and 2.4% of 3-phenoxybenzyl alcohol.

I claim:

1. A process for the preparation of insecticidal esters of m-phenoxybenzyl alcohol, α-cyano-m-phenoxybenzyl alcohol and α-ethynyl-m-phenoxybenzyl alcohol with 2,2-dimethylcyclopropanecarboxylic acids which comprises mixing a methyl or ethyl ester of the carboxylic acid, m-phenoxybenzyl alcohol α-cyano-m-phenoxybenzyl alcohol or α-ethynyl-m-phenoxybenzyl alcohol and a transesterification catalyst which is a titanium compound of the formula:

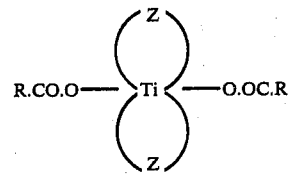

wherein R is a lower alkyl radical and Z is acetylacetone or ethyl acetoacetate, and heating the mixture at a temperature such that the methanol or ethanol are removed by distillation as it is formed.

2. A process as claimed in claim 1 wherein the reaction temperature is 80° to 160° C.

3. A process as claimed in claim 1 wherein the reaction is carried out in a solvent such that the reaction mixture boils at the desired reaction temperature so that the methanol or ethanol formed during the process is distilled off with a part of the solvent.

4. A process as claimed in claim 1 wherein the amount of catalyst used is at least 0.0005 mol per mol of carboxylic ester.

5. A process as claimed in claim 1 wherein the amount of catalyst used is from 0.001 to 0.2 mol per mol of carboxylic ester.

6. A process as claimed in claim 1 wherein the m-phenoxybenzyl alcohol or its α-cyano or α-ethinyl derivative and the methyl or ethyl ester of the carboxylic acid are used in equimolar proportions.

7. A process as claimed in claim 1 wherein the 2,2-dimethylcyclopropanecarboxylic acid is substituted in the 3-position by a 2',2'-dimethylvinyl, 2',2'-dichlorovinyl, 2'-ethinylvinyl, 2',2'-dibromovinyl, 2'-chloro-2'-trifluoromethylvinyl or 2',2'-bis(trifluoromethyl)vinyl group.

* * * * *